United States Patent [19]

Arai et al.

[11] Patent Number: 4,590,223

[45] Date of Patent: May 20, 1986

[54] PRODUCING POLYURETHANES USING HYDROXY-ALKYL PIPERAZINE CATALYST COMPOSITIONS

[75] Inventors: Shoji Arai, Yamaguchi; Masazumi Hasegawa, Kanagawa, both of Japan

[73] Assignee: Toyo Soda Manufacturing Co., Ltd., Shinnanyo, Japan

[21] Appl. No.: 748,140

[22] Filed: Jun. 24, 1985

Related U.S. Application Data

[63] Continuation of Ser. No. 601,915, Apr. 17, 1984, abandoned, which is a continuation of Ser. No. 476,705, Mar. 18, 1983, abandoned.

[30] Foreign Application Priority Data

Mar. 23, 1982 [JP] Japan .................................. 57-44625

[51] Int. Cl.$^4$ ...................... C08G 18/20; C08G 18/14; B01J 31/00; C07D 295/08
[52] U.S. Cl. .................................... 521/118; 502/167; 528/49; 252/182; 544/401
[58] Field of Search .......................... 521/118; 528/49; 502/167; 544/401

[56] References Cited

U.S. PATENT DOCUMENTS

4,379,757  4/1983  Baskent et al. ........................ 521/118

FOREIGN PATENT DOCUMENTS

3310124 10/1983 Fed. Rep. of Germany ...... 544/401
807750  1/1959 United Kingdom ................ 544/401
2144116A  2/1985 United Kingdom .

Primary Examiner—Herbert S. Cockeram
Attorney, Agent, or Firm—Cushman, Darby & Cushman

[57] ABSTRACT

Disclosed is a catalytic composition comprising a substance having the general formula:

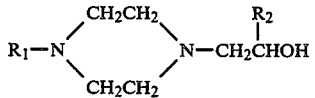

where $R_1$ is an alkyl group having 1 to 3 C atoms and $R_2$ is a group selected from —H, —$CH_3$ and $CH_2CH_3$.

The catalytic composition is odorless and excellent in the urethane forming reaction in production of polyurethane.

15 Claims, No Drawings

PRODUCING POLYURETHANES USING HYDROXY-ALKYL PIPERAZINE CATALYST COMPOSITIONS

This is a continuation of application Ser. No. 601,915, filed Apr. 17, 1984, which was abandoned upon the filing hereof which is a continuation of Ser. No. 476,705, filed Mar. 18, 1983 now abandoned.

BACKGROUND OF THE INVENTION

1. Field of the Invention

The present invention relates to novel tertiary amines which are useful as catalyst for producing flexible and rigid foams and elastomers of polyurethane. More particularly, this invention relates to novel amine catalysts which contain a hydroxyl group and are odorless and excellent in the urethane forming reaction when used for producing polyurethane.

2. Description of Prior Art

It is well known that the tertiary amines provide a good catalyst for producing polyurethane. In fact, a tertiary amine having a hydroxyl group, such as dimethylethanolamine, has been used as catalyst for producing polyurethane.

However, dimethylethanolamine has a degree of volatility with emission of an offensive odor, and also has disadvantages such as insufficient catalytic activities in the uretane forming reaction and cure.

SUMMARY OF THE INVENTION

The present inventors noticed the utility of tertiary amines having a hydroxyl group and intensively investigated for catalyst free from those disadvantages mentioned above. Thus, the present inventors finally succeeded in developing a novel amine catalyst which is odorless and excellent in the urethane forming reaction.

The novel catalyst of the present invention features pronounced activity in accelerating the urethane forming reaction for the production of polyurethane. As a result, the catalyst of this invention can be applied as catalyst for producing polyurethane from polyester polyol, for which morpholine catalysts have been hitherto used. Some kinds of the morpholine catalysts are known as being toxic. Therefore, use of the catalyst of the present invention can contribute to solve the problem of toxicity inherent to morpholine catalysts. It has been revealed, as an additional advantage, that the catalyst of this invention is possessed of the property as a thermo-sensitive catalyst in that the activity of this catalyst is increased when the temperature is increased as the chemical reaction progresses in the production of polyurethane.

Another feature of the novel catalyst of the present invention is that a flexible urethane foam prepared in the presence of the catalyst of this invention exhibits a small residual strain on wet compression set at the elevated temperature. Conventionally, a practical problem has often been confronted with that when a tertiary amine having a hydroxyl group, such as dimethylethanolamine, is used as catalyst, the residual strain on wet compression set at the elevated temperature which is an important physical property of a urethane foam, increases. Surprisingly, it has been found that a very small residual strain on wet compression can be obtained at the elevated temperature when the catalyst of this invention is used. This fact explicitly demonstrates that the use of catalyst of the present invention provides a urethane foam having good elongation properties without sacrificing any other property.

An additional feature of the novel catalyst of this invention is that it is odorless. This is due to the high boiling point, hence a relatively low volatility, of the catalyst and secondly due to the reactive hydroxyl group present in the molecule of the catalyst which makes the catalyst to be confined in the polyurethane resin without emitting offensive odor. This feature is very desirable from the standpoint of improving the working condition as well as preventing public pollution.

These remarkable features of the catalyst of the present invention indicated more peculiar advantages of this catalyst when used as catalyst in the production of polyurethane for flexible and rigid foams and elastomer.

DETAILED DESCRIPTION OF THE INVENTION

Hereinbelow the present invention will be described in more detail.

The novel amine catalyst of the present invention is a derivative of piperazine having a hydroxyl group, expressed by the following formula:

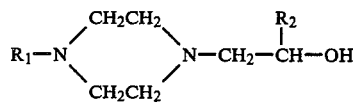

In the formula, $R_1$ is a methyl, ethyl or propyl group, preferably a methyl group. $R_2$ is a hydrogen atom, a methyl or ethyl group, preferably hydrogen or methyl.

The novel catalyst of the present invention can be easily prepared by the known 2-step reaction process. Namely, the first step reaction is to synthesize N-hydroxyalkylpiperazine by the reaction of piperazine with ethylene oxide, propylene oxide, or butane-1,2-oxide. The second step reaction is to convert the above product into a tertiary compound. For this reaction, may be utilized the Leuckart-Wallach reaction described in U.S. Pat. No. 4,026,840 and the reductive methylation reaction disclosed in West German Pat. No. 26 18 580.

According to the present invention, the amount of catalyst to be used in the production of polyurethane is 0.01 to 4 parts, preferably 0.05 to 3 parts, against 100 parts of polyol used. The catalyst may be used in combination with triethylenediamine and organic tin compounds which are usually employed as cocatalyst.

Polyisocyanate used in the production of polyurethane by using the catalyst of this invention is known and may be selected from the group consisting of tolylenediisocyanate, diphenylmethane diisocyanate, polymeric polyisocyanate and aliphatic polyisocyanate. Also the polyol to be used in the present invention is known polyesterpolyol or polyetherpolyol, which includes, for example, polyesterpolyols which are usually derived from a dibasic acid and a polyhydric alcohol, polyetherpolyols which are prepared by the addition reaction of a polyhydric alcohol, such as glycol, glycerine, pentaerythritol trimethylolpropane, and can sugar with ethyleneoxide or propyleneoxide, and amine polyols.

In the production of polyurethane may be added, if necessary, a foaming agent, such as $CFCl_3$ and $CH_2Cl_2$, a surfactant, such as organopolysiloxane, a flame retardant agent, such as halogenated alkyl compounds and halogenated phosphorus compounds, and other additives. Any type of these additives may be used in any amounts within the limits of the conventional forms and procedures.

The present invention will be more clearly understood from the following embodiments of the present invention in comparison with reference examples.

EXAMPLE FOR REFERENCE 1

Synthesis of N-hydroxyethylpiperazine

In a 3 liter round bottom flask provided with an agitator and a cooler, were placed 672 g of piperazine and 1600 ml of methanol. Holding the flask in a water bath, ethylene oxide gas was slowly bubbled into the solution in the flask. The temperature of the solution, which tended to elevate during the reaction, was kept at 15° to 25° C. with ice.

After 103 g of ethylene oxide was bubbled into the solution, the temperature of water bath was elevated to 60° C., and the solution was stirred for further one hour.

When the reaction was completed, the solution contained 503 g of unreacted piperazine and 130 g of N-hydroxyethylpiperazine, and 27 g of bis(N-hydroxyethyl)piperazine. 120 g of N-hydroxyethylpiperazine having boiling point from 121° to 123° C. under 10 mmHg was obtained by distillation of this reaction solution.

EXAMPLE FOR REFERENCE 2

Synthesis of N-(2-hydroxypropyl)piperazine

Using the same apparatus in Example for Reference 1, propylene oxide, instead of bubbling ethylene oxide, was added with a dropping funnel. After the completion of addition, the temperature of water bath was elevated to 60° C. N-(2-hydroxypropyl)piperazine having boiling point at 115° C. under 12 mmHg was obtained by distillation of this reaction solution.

EXAMPLE FOR REFERENCE 3

Tertiarization of N-hydroxyethylpiperazine

In a flask provided with a stirring device and a dropping funnel, 391 g of N-hydroxypiperazine prepared in Example for Reference 1 was slowly added in drops into a mixture of 207 g of formic acid and 20 g of water. The temperature of the mixture was elevated to 100° C. and 271 g of 36.6% formalin was added slowly in drops. The reaction mixture was refluxed until no more carbon dioxide was evolved. The solution was cooled and concentrated by evaporation with a rotary evaporator. A piece of solid sodium hydroxide was added to obtain an organic phase. This organic phase was transferred to a flask. Distillation by using a distillation tower separated N-methyl-N'-hydroxyethylpiperazine having a boiling point at 116° C. under 14 mmHg.

The chemical structure was ascertained by the elemental analysis, nuclear magnetic resonance spectrum, and mass spectrum analysis.

EXAMPLE FOR REFERENCE 4

N-methyl-N'-(2-hydroxypropyl)piperazine

By the same process as in Example for Reference 3, N-(2-hydroxypropyl)piperazine which was synthesized in Example for Reference 2 was recited to obtain N-methyl-N'-(2-hydroxypropyl)piperazine having a boiling point at 135° C. under 20 mmHg.

The chemical structure was ascertained by the elemental analysis, nuclear magnetic resonance spectrum and the mass spectrum analysis.

EXAMPLE 1

Raw materials were mixed in the proportion given below (formulation). Foaming was carried out following the ordinary handmade foaming procedure. Polyols, water, surfactant, catalyst and polyisocyanate were mixed under stirring and poured into an aluminum box of 25 cc capacity maintained at 40° C., to form a urethane foam. A part of the product was taken as specimen and physical properties were measured by specified methods. The results are shown in Table 1.

A urethane foam with good elongation property could be produced without increasing the residual strain on wet compression set at the elevated temperature, in comparison with the product in Example for Reference 1.

| Formulation: | Parts by weight | |
| --- | --- | --- |
| FA-703[1] | 68.0 | |
| FA-728[2] | 30.0 | Polyol |
| Diethanolamine | 2.0 | |
| Water | 2.5 | |
| L-5305[3] | 1.0 | |
| R-11[4] | 5.0 | |
| Catalyst | Varied | |
| Isocyanate[5] | Index 105 | |

[1]Polyetherpolyol having an average number of molecules 5,000, commercially available from Sanyo Kasei Kogyo K.K.
[2]Polymeric polyol commercially available from Sanyo Kasei Kogyo K.K. grafted acrylonitrile-styrene.
[3]Surfactant commercially available from Union Carbide Corporation.
[4]Freon 11
[5]A polyisocyanate mixture of 80 parts of tolylenediisocyanate (T-80) with 20 parts of polyisocyanate having 2.3 to 2.7 isocyanate groups (a polymerized diphenylmethanediisocyanate), both obtained from Japan Polyurethane Kogyo K.K.

TABLE 1

| Catalyst (parts) | | | | |
| --- | --- | --- | --- | --- |
| TEDA (L-33)[6] | 0.4 | 0.4 | 0.4 | 0.4 |
| N—methyl-N'—hydroxyethylpiperazine | 0.2 | 0.4 | 0.6 | 0.8 |
| Cream time (seconds) | 17.5 | 17.0 | 16.5 | 15.5 |
| Gel time (seconds) | 124 | 104 | 92 | 84 |
| Rise time (seconds) | 174 | 144 | 127 | 118 |
| Density (kg/m$^3$) | 44.1 | 42.3 | 41.6 | 40.6 |
| CLD 25% | 3.6 | 3.6 | 3.4 | 3.3 |
| 65% | 13.4 | 11.7 | 10.9 | 10.8 |
| Elongation (%) | 79 | 91 | 100 | 97 |
| Residual strain on wet compression set at the elevated temperature (%) | 18.2 | 16.2 | 17.8 | 19.6 |

[6]Triethylenediamine commercially available from Toyo Soda Manufacturing Co., Ltd. A liquid material containing 67% of dipropyleneglycol.

EXAMPLE FOR COMPARISON 1

The same foaming test as in Example 1 was carried out, using N-ethylmorpholine instead of N-methyl-N'-hydroxyethylpiperazine. Results are shown in Table 2.

TABLE 2

| Catalyst (parts) | | | | |
| --- | --- | --- | --- | --- |
| TEDA (L-33) | 0.4 | 0.4 | 0.4 | 0.4 |
| N—ethylmorpholine | 0.1 | 0.2 | 0.4 | 0.6 |
| Cream time (seconds) | 18.0 | 17.5 | 16.0 | 15.0 |
| Gel time (seconds) | 122 | 112 | 90 | 88 |
| Rise time (seconds) | 175 | 158 | 125 | 109 |
| Density (kg/m$^3$) | 43.2 | 43.2 | 41.5 | 42.7 |
| CLD 25% | 3.7 | 3.8 | 3.4 | 3.4 |
| 65% | 14.2 | 14.2 | 12.2 | 12.0 |

| TABLE 2-continued | | | | |
|---|---|---|---|---|
| Elongation (%) | 84 | 87 | 84 | 85 |
| Residual strain on wet compression set at the elevated temperature (%) | 17.6 | 18.3 | 17.0 | 19.6 |

EXAMPLE 2

Foaming was carried out with N-methyl-N'-(2-hydroxypropyl) piperazine instead of N-methyl-N'-hydroxyethyl piperazine in the same procedure as in Example 1 and test results are shown in Table 3, from which it is clearly understood that a urethane foam having good elongation can be obtained without increasing the residual strain on wet compression set at the elevated temperature just as in Example 1.

TABLE 3

| Catalyst (parts) | | | | |
|---|---|---|---|---|
| TEDA (L-33) | 0.4 | 0.4 | 0.4 | 0.4 |
| N—methyl-N'—(2-hydroxypropyl)piperazine | 0.2 | 0.4 | 0.7 | 0.9 |
| Cream time (seconds) | 17 | 16 | 15 | 13 |
| Gel time (seconds) | 125 | 112 | 100 | 93 |
| Rise time (seconds) | 175 | 156 | 141 | 130 |
| Density (kg/m³) | 41.2 | 41.8 | 40.2 | 41.8 |
| CLD 25% | 3.6 | 3.4 | 3.0 | 3.4 |
| 65% | 11.3 | 10.7 | 10.1 | 11.4 |
| Elongation (%) | 85 | 93 | 105 | 96 |
| Residual strain on wet compression set at the elevated temperature (%) | 17.7 | 19.5 | 20.5 | 20.2 |

What we claim:

1. A catalytic composition for producing polyurethane, comprising a substance of the following formula:

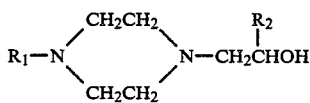

where $R_1$ is methyl and $R_2$ is a group selected from —H, —CH$_3$ and —CH$_2$CH$_3$.

2. A catalytic composition according to claim 1, in which the substance has the following formula

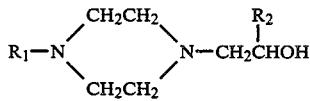

in which $R_1$ is a methyl group and $R_2$ is hydrogen or a methyl group.

3. A catalytic composition according to claim 1, in which the substance is N-methyl-N'-hydroxyethyl piperazine.

4. A catalytic composition according to claim 1, in which the substance is N-methyl-N'-(2-hydroxypropyl)piperazine.

5. A catalyst for producing polyurethane, having the following formula:

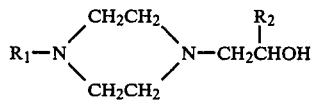

where $R_1$ is methyl and $R_2$ is a group selected from —H, —CH$_3$ and —CH$_2$CH$_3$.

6. A process of preparing a polyurethane comprising reacting a polyesterpolyol or a polyetherpolyol with a polyisocyanate in the presence of the catalyst of claim 5.

7. A process according to claim 6 wherein there is reacted a polyetherpolyol with a polyisocyanate.

8. A process of preparing a polyurethane comprising reacting a polyesterpolyol or a polyetherpolyol with a polyisocyanate in the presence of the catalyst of claim 2.

9. A process of preparing a polyurethane comprising reacting a polyesterpolyol or a polyetherpolyol with a polyisocyanate in the presence of the catalyst of claim 3.

10. A process of preparing a polyurethane comprising reacting a polyesterpolyol or a polyetherpolyol with a polyisocyanate in the presence of the catalyst of claim 4.

11. A process according to claim 6 wherein there is included a foaming agent and there is produced a foamed product.

12. A process according to claim 11 wherein the foaming agent is water.

13. A catalytic composition according to claim 1 including a triethylenediamine as a cocatalyst.

14. A process of preparing a polyurethane comprising reacting a polyesterpolyol or a polyetherpolyol with a polyisocyanate in the presence of the catalyst composition of claim 13.

15. A reaction mixture for producing polyurethane comprising (1) a substance of the following formula:

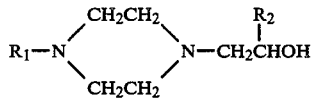

where $R_1$ is methyl and $R_2$ is a group selected from —H, —CH$_3$ and —CH$_2$CH$_3$, (2) a polyesterpolyol or polyetherpolyol and (3) a polyisocyanate.

* * * * *